United States Patent
Holmes et al.

(10) Patent No.: US 11,160,501 B2
(45) Date of Patent: Nov. 2, 2021

(54) PROCESSING OPTICAL COHERENCY TOMOGRAPHY SCANS

(71) Applicant: MICHELSON DIAGNOSTICS LTD., Kent (GB)

(72) Inventors: Jonathan Denis Holmes, Kent (GB); Richard Whitehead, Surrey (GB)

(73) Assignee: MICHELSON DIAGNOSTICS LIMITED

( * ) Notice: Subject to any disclaimer, the term of this patent is extended or adjusted under 35 U.S.C. 154(b) by 0 days.

(21) Appl. No.: 16/940,642

(22) Filed: Jul. 28, 2020

(65) Prior Publication Data

US 2020/0352502 A1 Nov. 12, 2020

Related U.S. Application Data (63) Continuation of application No. 16/060,692, filed as application No. PCT/GB2016/053887 on Dec. 9, 2016, now Pat. No. 10,758,181.

(30) Foreign Application Priority Data

Dec. 10, 2015 (GB) ..................................... 1521786

(51) Int. Cl.
*A61B 5/00* (2006.01)
*G06T 7/10* (2017.01)
*G06T 7/00* (2017.01)

(52) U.S. Cl.
CPC ............ *A61B 5/489* (2013.01); *A61B 5/0066* (2013.01); *G06T 7/0012* (2013.01); *G06T 7/10* (2017.01); *A61B 2576/02* (2013.01); *G06T 2207/10101* (2013.01); *G06T 2207/30088* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 10,489,906 B2* | 11/2019 | Holmes | G06T 7/0012 |
| 2015/0230708 A1 | 8/2015 | Wang et al. | |
| 2018/0018785 A1* | 1/2018 | Holmes | A61B 5/445 |

FOREIGN PATENT DOCUMENTS

WO 2014175853 A1 10/2014

OTHER PUBLICATIONS

International Search Report and Written Opinion pertaining to International Application No. PCT/GB2016/053887, dated Apr. 6, 2017, 17 pages.

(Continued)

*Primary Examiner* — Dov Popovici
(74) *Attorney, Agent, or Firm* — Burns & Levinson LLP; Steven M. Mills (57) ABSTRACT

A method of and apparatus for processing optical coherence tomography (OCT) scans through a subject's skin. The method includes receiving at least one OCT scan through the subject's skin, each scan representing an OCT signal in a slice through the subject's skin. Each OCT scan is processed so as to determine the presence of at least one blood vessel in each scan. A diameter is determined of at least one of the at least one blood vessels whose presence has been determined. A depth profile is determined of blood vessel density for different vessel diameters.

10 Claims, 6 Drawing Sheets

(56) References Cited

OTHER PUBLICATIONS

IPO Search Report pertaining to Application No. GB1521786.2, dated May 9, 2016, 4 pages.
Enfield et al., "In vivo imaging of the microcirculation of the volar forearm using correlation mapping optical coherence tomography (cmOCT)," Biomedical Optics Express, vol. 2, No. 5, Apr. 13, 2011, pp. 1184-1193.
Liew et al., "In vivo assessment of human burn scars through automated quantification of vascularity using optical coherence tomography," International Society for Optical Engineering, vol. 18(6), Nov. 22, 2012, 10 pages.
Sihan et al., "Fully Automatic Three-Dimensional Quantitative Analysis of Intracoronary Optical Coherence Tomography: Method and Validation," Catheterization and Cardiovascular Interventions, 74: pp. 1058-1065 (2009).
Shengxian et al., "In vivo comparison of arterial lumen dimensions assessed by co-registered three-dimensional (3D) quantitative coronary angiography, intravascular ultrasound and optical coherence tomography," Int J Cardiovasc Imaging (2012) 28: pp. 1315-1327.
Zhou et al., "Imaging of skin microvessels with optical coherence tomography: potential uses in port wine stains," Experimental and Therapeutic Medicine 4: 2012, pp. 1017-1021.

\* cited by examiner

PROCESSING OPTICAL COHERENCY TOMOGRAPHY SCANS

RELATED APPLICATIONS

This application is a continuation of U.S. patent application Ser. No. 16/060,692 filed on Jun. 8, 2018, which is a U.S. national stage application under 35 U.S.C. § 371 of PCT Application No. PCT/GB2016/053887 filed on Dec. 9, 2016, which is published in English under PCT Article 21(2) as WO 2017/098262 on Jun. 15, 2017, which in turn claims the benefit and priority to the Great Britain Patent Application No. 1521786.2, filed on Dec. 10, 2015. The entire contents of each of which are incorporated herein in their entirety by reference for all purposes.

This invention relates to a method of processing optical coherence tomography (OCT) scans, and associated apparatus.

There is a need for rapid non-invasive assessment of the vascular network in a subject's skin, as an aid to planning and guiding treatments for aesthetic and medical conditions affecting patients, for example (but not limited to) port wine stains, hemangiomas, hypertrophic scars, rosacea, and 'spider veins'. Typical treatments for these conditions producing temporary or permanent effects on the vascular network in the dermis include systemic and topically applied drugs, and laser treatments. These treatments either cause the blood vessels and capillaries to constrict, or they damage the vessels to reduce or terminate their ability to transport blood.

When deciding on the type of treatment, and then planning the treatment regime, it is of critical importance to correctly assess the characteristics of the vascular network. For example, laser treatments are designed to deliver a certain amount of energy to the target vessels to damage them; if the energy of the pulse is too high then the surrounding tissue will be damaged, which may result in undesirable scarring and pain; conversely if the energy pulse is too low, then the treatment will be ineffective and will have to be repeated (perhaps multiple times) to achieve the desired impact. The laser pulse characteristic can be tuned to achieve a desired energy delivery profile [RR Anderson, J A Parrish, Selective Photothermolysis: Precise Microsurgery by Selective Absorption of Pulsed Radiation, Science, 220 (4596), 1983, pp 524-527], but the clinician must know the vessel characteristics in order to set this up for optimal results.

Various devices have been available for some time that measure certain aspects of the vascular network in the skin. Examples include for example visible and infra-red cameras (e.g. Visia (www.canfieldsci.com)), and laser Doppler imaging (www.moorinstruments.com).

However, these devices suffer from key disadvantages, including:

The measurements take too long to capture and/or to analyse;

The results can be subjective and require a high degree of specialist knowledge to interpret;

The measurements are of the skin surface only and do not capture the depth of the vessels or their diameter or density;

The devices are cumbersome to use or set up.

Recently, optical scanning techniques such as optical coherence tomography (OCT) have been successfully applied to imaging the sub-surface of the skin in a rapid noninvasive manner for applications in clinical dermatology [Schmitz, 1., et al. (2013) "Optical coherence tomography: its role in daily dermatological practice" German Society of Dermatology.]. Most recently, advances in OCT technology have allowed us to detect and measure the vascular network in the upper dermis, as shown in our co-pending United Kingdom patent application, no GB1503196.6, and in skin lesions [N. de Carvalho et al., In vivo micro-angiography by means of speckle-variance optical coherence tomography (SV-OCT) is able to detect microscopic vascular changes in naevus to melanoma transition, JEADV (2015). Furthermore, as described in the PCT patent application published as WO2015/001317, it is possible to extract from OCT data, the skin surface topography with a high degree of accuracy and thereby derive and output skin roughness, another parameter of interest to the manufacturers of skin care products.

Optical Coherence Tomography (OCT) was invented in 1991 at the Massachusetts Institute of Technology in the United States of America and is commonly used for imaging human tissue of various organs, in particular the eye, and also skin (J. Welzel, "Optical coherence tomography in dermatology: a review," Skin Research and Technology, vol. 7, pp. 1-9, 2001). In particular, we are aware of the VivoSight® OCT device, manufactured and marketed by Michelson Diagnostics Ltd of Orpington, Kent, United Kingdom, which is designed for use by professional dermatologists in the assessment of skin lesions of patients.

The VivoSight OCT device scans the skin and presents to the user images of the skin subsurface structure, in a plane perpendicular to the skin surface (By convention, the OCT device is assumed to be positioned vertically above the skin surface). The resulting two-dimensional image is commonly known in the art as a "B-scan", and comprises many lines of vertical pixels commonly known in the art as "A-lines".

Each pixel in the image has a value corresponding to the signal obtained from the OCT device resulting from the skin optical properties at the y-position for that pixel. Also, the VivoSight device can acquire scans at multiple locations across the skin surface in order to build up a series of B-scans across a lesion of interest. This is known in the art as a multi-slice "stack" and can be viewed by the user in a variety of ways to elicit tissue features of medical interest such as nests of cancer cells.

For example, the user can view the stack of B-scans in rapid succession to fly through a lesion area. Also, the stack of data can be re-sampled so that one or more image slices in the horizontal plane (perpendicular to the B-scans) can be extracted and viewed. Horizontal slices are sometimes known in the art as "C-scans". Thus, the C-scan at any desired depth can be viewed. Furthermore, a C-scan and B-scan from a stack can be viewed simultaneously. All of this is well known to those skilled in the art of OCT and more generally medical imaging.

According to a first aspect of the invention, there is provided a method of processing optical coherence tomography (OCT) scans through a subject's skin, the method comprising:

receiving at least one OCT scan through the subject's skin, each scan representing an OCT signal in a slice through the subject's skin;

processing each OCT scan so as to determine the presence of at least one blood vessel in each scan;

determining a diameter of at least one of the at least one blood vessels whose presence has been determined.

Up until now, no device has been developed that can in one scan procedure capture, process and display key skin vasculature data including, but not limited to, individual blood vessel diameter. We have appreciated the utility of such a device in characterising a vascular network, particularly in the assessment of, for example (but not limited to) port wine stains, hemangiomas, hypertrophic scars, rosacea, and 'spider veins'.

The method may further comprise determining a depth of the blood vessels, typically through the subject's skin. The method may comprise determining a depth profile of blood vessel density for different vessel diameters, typically for a plurality of ranges of vessel diameters. In order to determine the depth of the blood vessels through the subject's skin, the method may comprise determining the position of the surface of the subject's skin in each scan.

The method may comprise capturing the scans using an OCT probe, and delivering a pulse of laser energy to a volume of the subject's skin comprising at least one blood vessel using the probe. The user may be able to select at least one of the energy, fluence and duration of the pulse depending upon the measurements of blood vessel diameter already made.

According to a second aspect of the invention, there is provided an optical coherence tomography (OCT) image processing apparatus, comprising a processor, a display coupled to the processor and storage coupled to the processor, the storage carrying program instructions which, when executed on the processor, cause it to carry out the method of the first aspect of the invention.

The image processing apparatus may comprise an OCT apparatus by means of which the OCT scans are captured. As such, the image processing apparatus may comprise an OCT probe arranged to generated interferograms, and the processor may be arranged to generate the images from the interferograms. As such, the image processor may be arranged to process the images as they are captured.

Furthermore, the OCT probe may be arranged so as to deliver a pulse of laser energy to a volume of the subject's skin comprising at least one blood vessel. The OCT apparatus may comprise a laser pulse source, having at least one control by means of which a user can select at least one of the energy, duration and fluence of the laser pulse; typically, a user would do this in response to the measurements of blood vessel diameter already made.

Alternatively, the image processing apparatus may be separate from any OCT apparatus and may be arranged to process the images subsequent to their capture. As such the image processing apparatus may comprise data reception means (such as a network connection or media drive) arranged to receive the images for processing.

There now follows, by way of example only, description of embodiments of the invention, described with reference to the accompanying drawings, in which.

Figure 1:
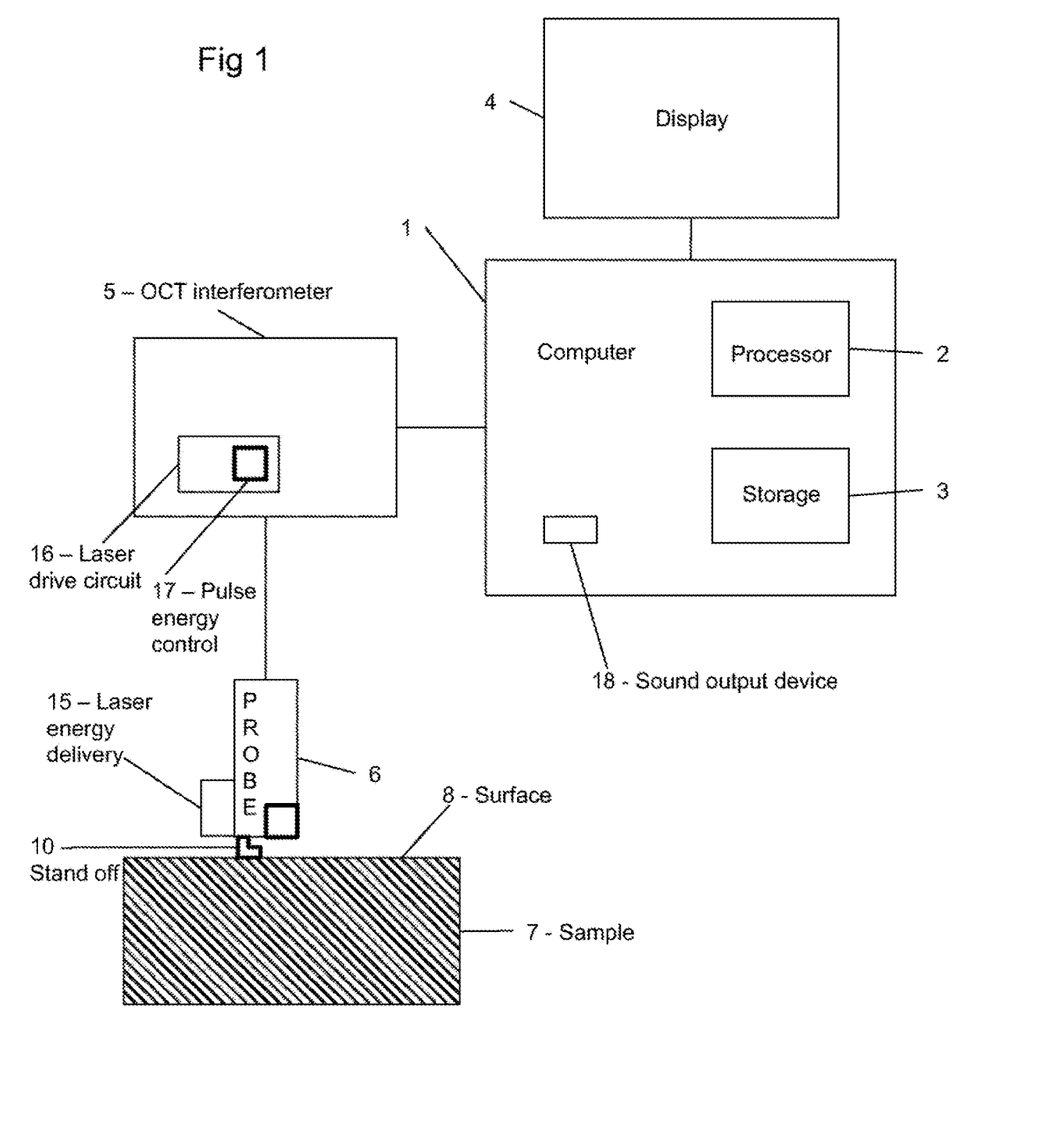
FIG. 1 shows schematically an optical coherence tomography (OCT) apparatus in accordance with an embodiment of the invention.

An optical coherence tomography (OCT) apparatus in accordance with an embodiment of the invention is shown in FIG. 1 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft® Windows® or Apple® Mac OS X® can be used. The computer 1 is also provided with a display 4 controlled by the processor 2 on which any desired graphics can be displayed, and a sound output device 18 such as a buzzer which can sound an alert noise.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight® apparatus available from Michelson Diagnostics of Orpington, Kent, United Kingdom. A stand-off 10 can be provided which spaces the probe 6 from the subject's skin 7.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin. By taking multiple scans spaced apart perpendicularly to the scans—and so parallel to the skin—a stack of scans can be formed, covering a volume of the subject's skin.

The OCT apparatus takes multiple scans spaced apart in time. Successive images from the same location on a subject's skin can be used to determine the presence of blood flow through blood vessels, by determining areas that have changed between successive images. Such changes can indicate the flow of blood cells through blood vessels. Our preferred technique is speckle decorrelation OCT as described in "In vivo imaging of the micro circulation of the volar forearm using correlation mapping optical coherence tomography (cmOCT)", J Enfield, E Jonathan and M Leahy, Biomed Opt Express. May 1, 2011; 2(5): 1184-1193, but we can also use speckle variance, differencing of intensity or phase, or any other computational technique.

The time interval between the different times should be carefully selected. If the time interval is too short, then there is not enough time for blood to move through the region to make a detectable change. If the time interval is too long, then gross movements of the probe relative to the skin make it difficult or impossible to ensure that the region in the second image is exactly the same location as the region in the first image, and this results in noise in the image. In human skin, a time interval of 3.5 milliseconds works well.

Figure 2:
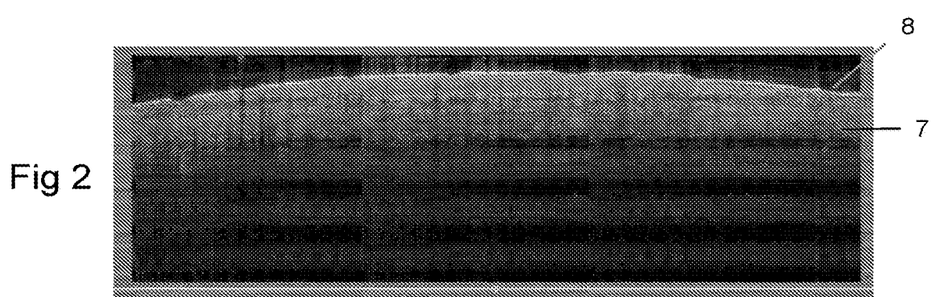
FIG. 2 shows an OCT scan of healthy tissue.
Figure 3:
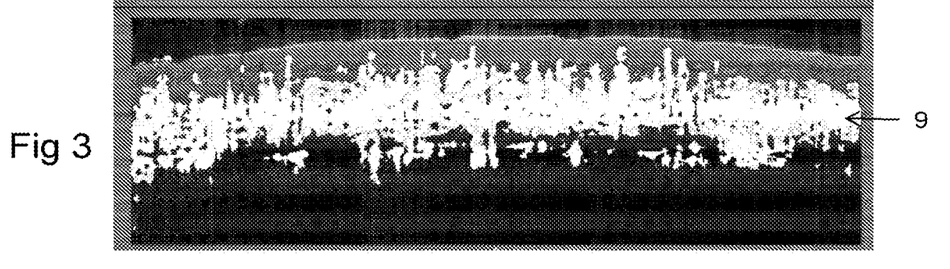
FIG. 3 shows the areas of movement in the OCT scan of FIG. 2.
Figure 4:
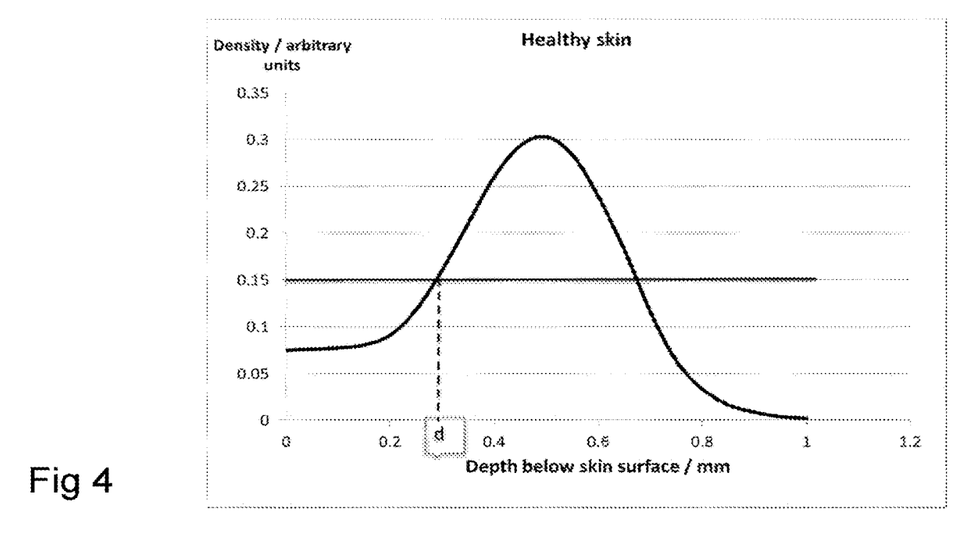
FIG. 4 shows an exemplary graph of density of varying areas with depth through healthy skin.

An example OCT scan is shown at FIG. 2, which shows a subject's skin 7, which has a surface 8. The results of comparing this to a successive image in healthy tissue are shown in FIG. 3, where areas of large differences are shown as white as indicated generally at 9. These areas represent areas where there are blood vessels. Typically, any area where change is determined at above a given threshold is determined to be a changing area.

The method also determines the skin surface topography, and therefore the depth of any detected sub-surface feature below the skin. In order to do so, the skin surface position must be found using the method shown in FIG. 5. In step 20, the stack of scans referred to above is generated. At step 22, in the preferred embodiment, the image data is filtered to reduce or remove random noise inherent of the coherent detection technique ('speckle noise') and other image artefacts particular to the imaging system used to capture the image data. The reduction in the effect of noise upon image contrast is achieved using linear and non-linear filtering techniques, intended to preserve edge features while removing speckle. Examples of such filters include linear filters, Kalman filters (see, for example, Igor Gurov and Maxim Volynsky "Recurrence signal processing in Fourier-domain optical coherence tomography based on linear Kalman filtering", Proc. SPIE 8792, Optical Methods for Inspection, Characterization, and Imaging of Biomaterials, 879203 (May 23, 2013); doi:10.1117/12.2020615; http://dx.doi.org/10.1117/12.2020615) or wavelet filters (see, for example, "Speckle reduction in optical coherence tomography images of human finger skin by wavelet modified BM3D filter", Bo Chong, Yong-Kai Zhu, Optics Communications Volume 291, 15 Mar. 2013, Pages 461-469, http://dx.doi.org/10.1016/j.optcom.2012.10.053).

Figure 5:
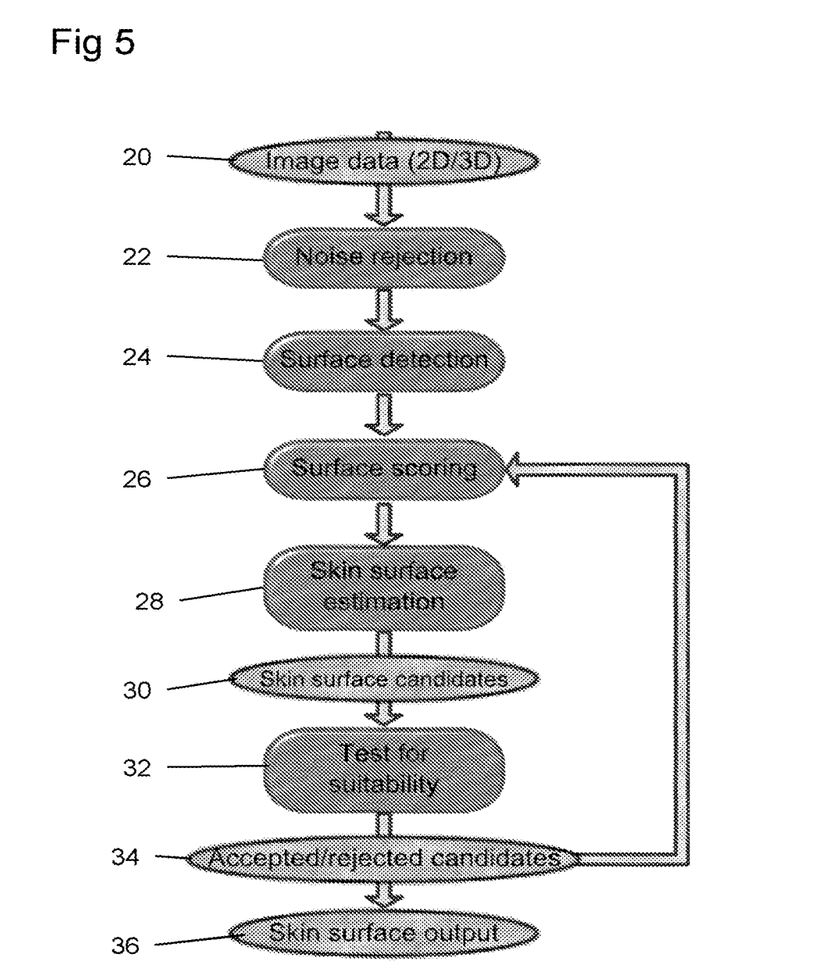
FIG. 5 shows a flowchart depicting how the apparatus of FIG. 1 determines the position of the skin surface.

The unadulterated proximal tissue surface represents a refractive index change from that of air to that of tissue and therefore presents a very strongly backscattering feature and high signal in OCT images. At step 24, to obtain candidates for skin surfaces in images, therefore, the image A-lines are filtered to indicate extrema in the OCT signal; certain of these are rejected based on simple parameters (position, classification and the local environment of the extrema, such as the difference between the positions of the extrema in adjacent images). Further edge-filtering may be employed to refine results and ensure that the estimations of skin surface are minimally affected by remaining speckle or a poorly-backscattering skin surface (in the presence of, for example, media which reduces or minimises the difference in refractive index at the proximal side of the skin surface).

The result of this stage is a 3D binary array of possible surface positions, with multiple solutions possible in each A-scan of the data array.

The process in step 24 may typically result in multiple candidates for the proximal skin surface. Step 26 is undertaken therefore to assign a score to each candidate in each A-scan according the probability that it does not represent the true skin surface. This algorithm may involve multiple independent estimates of probability and combine these in a suitable manner to provide a meaningful metric.

In step 28, the set of multiple skin surface candidates and their weights are then processed to select a set of candidates 30 representing a single surface. The algorithm employed to select this surface attempts to minimise the sums of the weights of candidates in the selected surface and also a weight assigned to the Euclidean distance between neighbouring candidates in the selected surface.

In step 32, the surface 30 selected in step 28 is assessed for suitability according to criteria based on a-priori knowledge of skin morphology, the result of this assessment is termed herein "the worthiness" of the surface. The criteria may include uniformity, periodicity of variation, surface variance amongst other factors, all being within expected limits from known skin samples. If an insufficient worthiness is attained, according to a prescribed value, the solution is rejected (at step 34) and steps 26, 28 and 32 repeated using an additional weighting factor derived in this step. The additional weighting assigned to the multitude of candidates in the repeated step 28 may be calculated based on the position of the surface and its overall worthiness as well as localised contribution to the worthiness of particular candidates.

After performing the steps of detecting time-varying regions that correspond to blood vessels, and of finding the skin surface topography, it is then possible to perform further useful processing steps as follows.

Figure 6:
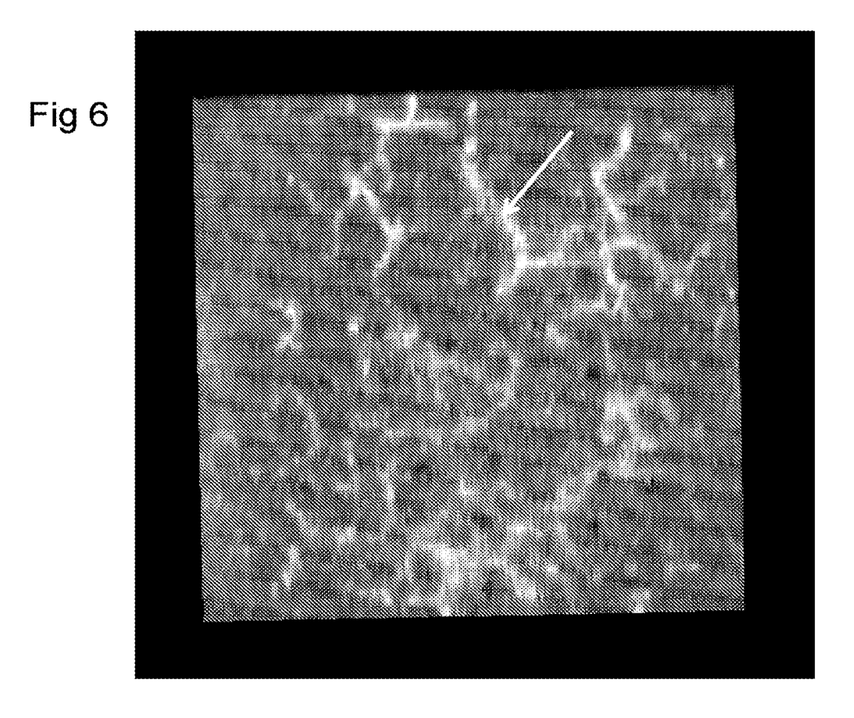
FIG. 6 shows how an exemplary C-scan would be displayed to a user in an embodiment of the invention.
Figure 7:
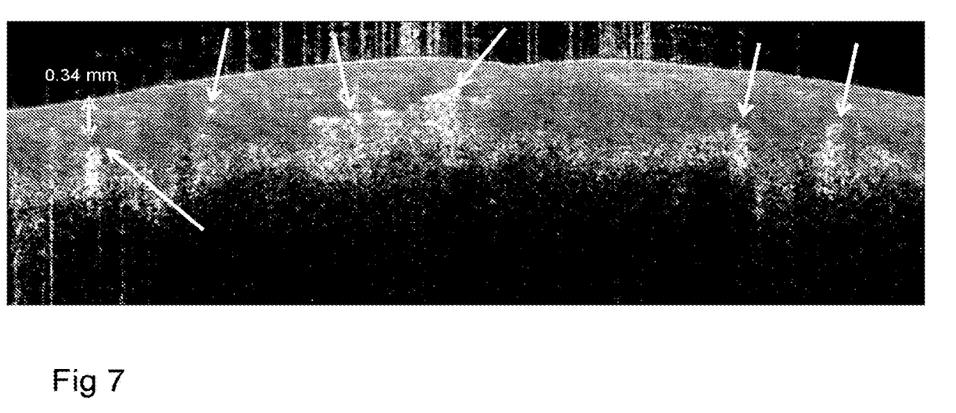
FIG. 7 shows how an exemplary B-scan would be displayed to a user in an embodiment of the invention.

In one aspect of the invention, the data is displayed to the user in either en-face (C-scan, as shown in FIG. 6 of the accompanying drawings) or vertical (B-scan, as shown in FIG. 7 of the accompanying drawings) format, or in a 3D rendering, and the user is provided with means to select any desired vessel by means of a mouse, trackball, trackpad or other device, depicted by the white arrows in FIGS. 6 and 7. Typically, a user might be able to select the depth through the subject's skin and display a C-scan, or a position through the subject's skin and display a B-scan. A vessel can then be selected using the mouse and processed to extract the vessel diameter at the pointed-to location. For example, the arrowed vessel in FIG. 6 is measured to be 170 microns (micrometres) in diameter. This is useful if a user wishes to "hit" a particularly large vessel.

For B-scans, the system can display the depth below the skin surface at that position (for example, the left-most arrowed vessel in FIG. 7 is 0.34 mm below the surface). Thus, the user is provided with a quick and easy means to characterize the properties of vessels that they wish to treat.

Further, the processing means may divide the scanned volume into a series of slices of pre-selected depth ranges below the surface, for example 0.0-0.1 mm, 0.1-0.2 mm and so on, and then analyze the vessels within each slice, so as to provide the user with quantification of the vessels at a particular depth range. This analysis may include, for example:

The volume of all vessels, within the slice

The volume of vessels in each of a pre-selected range of vessel diameters, within the slice The mean and the median diameter of vessels in the slice The diameter and length of the largest vessel in the slice These parameters may then be displayed to the user in order to enable optimizing of the laser pulse energy (or other treatment decision). For example, the system may calculate the median or mean vessel diameter and depth, and then set the laser pulse energy, fluence and duration from a look-up table.

The OCT probe can be integrated with a laser energy delivery device 15, so that the user can instantly treat the scanned area with a laser pulse of chosen energy, created at laser drive circuit 16 which itself has pulse energy control 17, without having to move the probe.

We have found that users are able to see a subject's vessel network and gauge the diameter and depth of the main vessels they want to treat and can then set their laser accordingly. This results in more effective treatment, in practice overall higher success rates, improved cosmetic results, and reduced number of treatment cycle needed.

The invention claimed is:

1. A method of processing optical coherence tomography, OCT, scans through a subject's skin, the method comprising:

receiving a plurality of OCT scans through the subject's skin, each scan representing an OCT signal in a slice through the subject's skin, the slice having depth below the subject's skin, the slices together forming a volume within the subject's skin;

processing each OCT scan so as to determine a presence of blood vessels in each scan;

dividing the volume into a plurality of depthwise slices and determining an average diameter of the blood vessels for each depthwise slice.

2. The method of claim 1, in which the depthwise slices are at predetermined depths.

3. The method of claim 2, in which the method comprises determining a position of a surface of the subject's skin in each scan, in which the predetermined depths are depths below the surface of the subject's skin.

4. The method of claim 1, comprising capturing the scans using an OCT probe, and delivering a pulse of laser energy to the volume within the subject's skin comprising at least one blood vessel using the probe.

5. The method of claim 1, carried out by an OCT image processing apparatus.

6. An optical coherence tomography, OCT, image processing apparatus, comprising a processor, a display coupled to the processor and storage coupled to the processor, the storage carrying program instructions which, when executed on the processor, cause it to carry out the method of claim 1.

7. The apparatus of claim 6, comprising an OCT apparatus by means of which the OCT scans are captured.

8. The apparatus of claim 7, in which the image processing apparatus comprises an OCT probe arranged to generate interferograms, and the processor is arranged to generate the scans from the interferograms.

9. The apparatus of claim 8, in which the OCT probe is arranged so as to deliver a pulse of laser energy to the volume within the subject's skin comprising at least one blood vessel.

10. The apparatus of claim 9, in which the OCT apparatus comprises a laser pulse source, having at least one control by means of which a user can select at least one of an energy, a fluence and a duration of the pulse of laser energy.

* * * * *